United States Patent [19]

Hatanaka et al.

[11] Patent Number: 5,167,958
[45] Date of Patent: Dec. 1, 1992

[54] WS7622A, B, C AND D SUBSTANCES, DERIVATIVES THEREOF, PROCESSES FOR PREPARATION THEREOF AND USE FOR TREATMENT OF PULMONARY EMPHYSEMA AND ADULT RESPIRATORY DISTRESS SYNDROME

[75] Inventors: Hiroshi Hatanaka, Kitasouma; Masami Ezaki, Tsukuba; Eisaku Tsujii, Tsukuba; Masanori Okamoto, Tsukuba; Nobuharu Shigematsu, Tsukuba; Masakuni Okuhara, Tsukuba; Shigehiro Takase, Tsukuba, all of Japan

[73] Assignee: Fujisawa Pharmaceutical Company, Ltd., Osaka, Japan

[21] Appl. No.: 645,820

[22] Filed: Jan. 25, 1991

Related U.S. Application Data

[63] Continuation of Ser. No. 482,822, Feb. 21, 1990, Pat. No. 5,021,240.

[30] Foreign Application Priority Data

| Mar. 14, 1989 | [GB] | United Kingdom | 8905817 |
| Sep. 11, 1989 | [GB] | United Kingdom | 8920485 |
| Sep. 18, 1989 | [GB] | United Kingdom | 8921078 |
| Oct. 2, 1989 | [GB] | United Kingdom | 8922164 |

[51] Int. Cl.$^5$ ............................................. A61K 35/00
[52] U.S. Cl. .................................................. 424/118
[58] Field of Search ................ 424/118, 123; 435/170

[56] References Cited

PUBLICATIONS

Cross et al., V. Iizuka 224 USPQ739 (1985).
Gminski, "Anti-elastin . . . " Biomed. Biochem Acta 50:87 (1991).
Powers, "Elastase . . . " Am. Rev. Res Dis 134:1097 (1986).
Idell, "Neutrophil . . . " Am. Rev. Res Dis 132:1098 (1985).
Schalkwijk, "Skin-derived . . . " Bio Chem. Bio Phys. Acta 1096:148 (1991).
Kuraumitsu, "Plasma . . . " Rheumatology 10:51 (1990).
Lehnert, "Relationship . . . " Surgery 172:345 (1991).
Velvart, "Degradation . . . " Rheumatology 7:195 (1987).
Glinski, "Basement . . . " Arh. Dermat Res 282:506 (1990).
Watanabe, "Human . . . " J. Biochem 108:753 (1990).

Primary Examiner—Frederick E. Waddell
Assistant Examiner—Gregory Hook
Attorney, Agent, or Firm—Oblon, Spivak, McClelland, Maier & Neustadt

[57] ABSTRACT

A method of treating pulmonary emphysema or adult respiratory distress syndrome in a subject in need thereof which comprises administering to the subject an effective amount of WS7622A, B, C and/or D, derivatives thereof, or their pharmaceutically acceptable salt.

1 Claim, 12 Drawing Sheets

WS7622A, B, C AND D SUBSTANCES, DERIVATIVES THEREOF, PROCESSES FOR PREPARATION THEREOF AND USE FOR TREATMENT OF PULMONARY EMPHYSEMA AND ADULT RESPIRATORY DISTRESS SYNDROME

This is a continuation of application Ser. No. 07/482,822, filed on Feb. 21, 1990 now U.S. Pat. No. 5,021,240.

This invention relates to new WS7622A, B, C and D substances and derivatives thereof.

More particularly, this invention relates to new WS7622A, B, C and D substances, derivatives thereof and their pharmaceutically acceptable salts which have an human leukocyte elastase-inhibiting activity, to processes for preparation thereof, and to a pharmaceutical composition comprising the same and to a method of use thereof.

The WS7622A, B, C and D substances can be produced by culturing a WS7622A, B, C and D substances-producing strain of the genus Streptomyces in a nutrient medium.

THE MICROORGANISM

The microorganism which can be used for the production of WS7622A, B, C and D substances is a WS7622A, B, C and D substances-producing strain belonging to the genus Streptomyces, among which *Streptomyces resistomycificus* No. 7622 has been newly isolated from a soil sample collected at Hirono-cho, Fukushima-ken, Japan.

A lyophilized sample of the newly isolated *Streptomyces resistomycificus* No. 7622 was firstly deposited with International Depositary Authority under the Budapest Treaty, the Fermentation Research Institute, Agency of Industrial Science and Technology (1-3, Higashi 1 chome, Tsukuba-shi, Ibaraki-ken, 305 Japan) under the accession number of FERM P-2306 (the deposited date: Feb. 23, 1989), as Streptomyces sp. No. 7622, and then this strain was named as *Streptomyces resistomycificus* No. 7622.

It is to be understood that the production of the novel WS7622A, B, C and D substances is not limited to the use of the particular organism described herein, which is given for the illustrative purpose only. This invention also includes the use of any mutants which are capable of producing WS7622A, B, C and D substances including natural mutants as well as artificial mutants which can be produced from the described organism by conventional means such as irradiation of X-ray, ultra-violet radiation, treatment with N-methyl-N'-nitro-N-nitrosoguanidine, 2-aminopurine, and the like.

The *Streptomyces resistomycificus* No. 7622 has the following morphological, cultural, biological and physiological characteristics.

(1) Morphological Characteristics:

The methods described by Shirling and Gottlieb [1] were employed for this taxonomic study.

Morphological observations were made with light and electron microscopes on cultures grown at 30° C. for 14 days on oatmeal agar, yeast extract-malt extract agar and inorganic salts-starch agar.

The vegetative mycelium developed well without fragmentation. The aerial mycelium branched monopodially and formed spiral chains and rectus-flexibilis chains of spores with more than 30 spores per chain. The spores had a smooth surface and were oval in shape with a size of 0.7–0.9×0.8–1.1 μm. Sclerotic granules, sporangia and zoospores were not observed.

Figure 1:
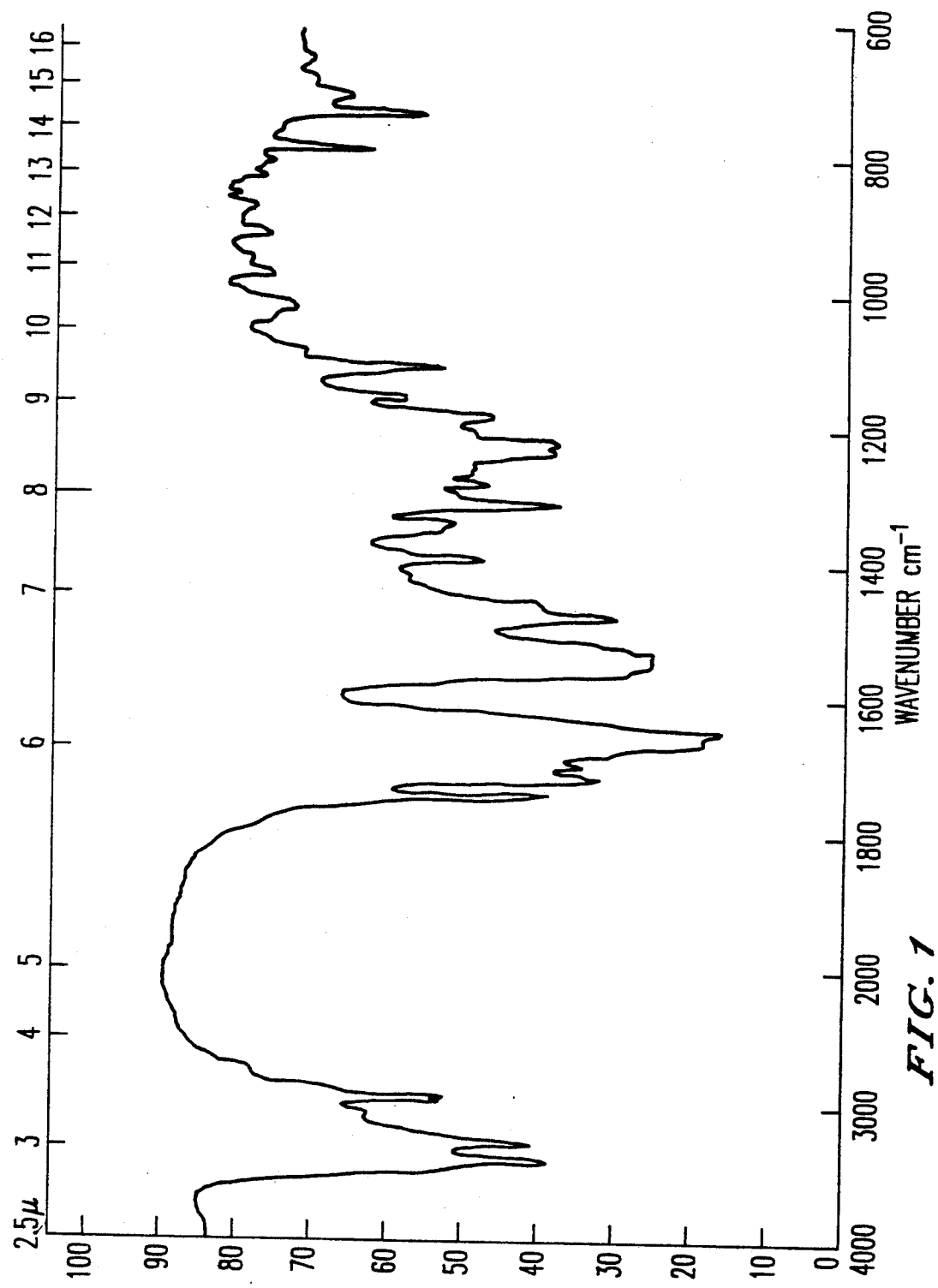
FIG. 1 is an infrared absorption spectrum of WS7622A.

(2) Cultural Characteristics:

Cultural characteristics were observed on ten kinds of media described by Shirling and Gottlieb as mentioned above, and by Waksman [2].

The incubation was carried out at 30° C. for 21 days. The color names used in this study were taken from Methuen Handbook of Colour [3]. The results are shown in Table 1.

TABLE 1

| Cultural characteristics of the strain No. 7622 | |
|---|---|
| Medium | Cultural characteristics |
| Yeast extract-malt extract agar | G: good<br>A: moderate, bluish gray(22E2)<br>R: brown(6F4)<br>S: none |
| oatmeal agar | G: good<br>A: moderate, bluish gray(22D2)<br>R: brown(6F6)<br>S: none |
| inorganic salts-starch agar | G: good<br>A: abundant, brownish gray(7E2)<br>R: violet brown(11F6)<br>S: none |
| glycerin-asparagine agar | G: good<br>A: abundant, brownish gray(6E2)<br>R: grayish orange(5B5)<br>S: none |
| peptone-yeast extract-iron agar | G: moderate<br>A: none<br>R: brown(6F6)<br>S: dark brown |
| tyrosine agar | G: good<br>A: poor, turquoise gray(24E2)<br>R: dark brown(7F8)<br>S: none |
| glucose-asparagine agar | G: moderate<br>A: none<br>R: yellowish white(4A2)<br>S: none |
| nutrient agar | G: poor<br>A: none<br>R: yellowish white(4A2)<br>S: none |
| Bennet agar | G: good<br>A: poor, bluish gray(22E3)<br>R: brownish orange(5C5)<br>S: none |
| sucrose-nitrate agar | G: good<br>A: none<br>R: grayish Magenta(13D4)<br>S: none |

Abbreviation:
G = growth, A = aerial mycelium, R = reverse side color, S = soluble pigment The aerial mycelium was bluish gray to brownish gray. Reverse side of growth was brown on yeast extract-malt extract agar and oatmeal agar, violet brown on inorganic salts-starch agar, and grayish Magenta on sucrose-nitrate agar. Melanoid pigments were produced, but other soluble pigments were not produced.

(3) Cell wall type:

The cell wall analysis was performed by the methods of Becker et al[4] and Yamaguchi[5].

Analysis of whole cell hydrolysates of strain No. 7622 showed the presence of LL-diaminopimelic acid. Accordingly, the cell wall of this strain is classified as type I.

(4) Biological and physiological properties:

Physiological properties and utilization of carbon sources are shown in Tables 2 and 3, respectively.

Temperature range for growth was determined on yeast-malt extract agar using a temperature gradient incubator TN-3 (made by Advantec Toyo Co., Ltd.).

Utilization of carbon sources was examined according to the method of Pridham and Gottlieb[6].

TABLE 2

Physiological properties of strain No. 7622

| Conditions | Characteristics |
| --- | --- |
| temperature range for growth | 12° C.–34° C. |
| optimum temperature for growth | 27° C. |
| gelatin liquefaction | positive |
| milk coagulation | negative |
| milk peptonization | positive |
| starch hydrolysis | positive |
| production of melanoid pigments | positive |
| decomposition of cellulose | negative |
| NaCl tolerance | >3% and <4% |

TABLE 3

Carbon utilization of the strain No. 7622

| Compounds | Growth |
| --- | --- |
| D-glucose | + |
| sucrose | + |
| D-xylose | ± |
| D-fructose | + |
| L-rhamnose | + |
| raffinose | − |
| L-arabinose | + |
| inositol | + |
| mannitol | + |

+: utilization
±: doubtful utilization
−: no utilization

Based on the morphological and physiological characteristics described above, strain No. 7622 is considered to belong to the genus Streptomyces.[7]

So, strain N. 7622 was compared with Streptomyces species described in literature.[8-12] As a result, it was found that the strain proved to closely resemble Streptomyces resistomycificus IF012814 in detail. There, it was found that the properties of both strains were almost identical except a few differences.

Table 4 shows the differences between the two strains.

TABLE 4

Differences between strain No. 7622 and Streptomyces resistomycificus IF012814

| Conditions | Characteristics | |
| --- | --- | --- |
| | IF012814 | No. 7622 |
| growth on sucrose-nitrate agar | poor | good |
| utilization of sucrose | no utilization | utilization |
| temperature range for growth | 14–37° C. | 12–34° C. |

TABLE 4-continued

Differences between strain No. 7622 and Streptomyces resistomycificus IF012814

| Conditions | Characteristics | |
| --- | --- | --- |
| | IF012814 | No. 7622 |
| NaCl tolerance | >4% and <6% | >3% and <4% |

It is considered to be proper that these differences are too small to regard strain No. 7622 as a different species.

Therefore, we identified the strain as Streptomyces resistomycificus and designated it Streptomyces resistomycificus No. 7622.

1) Shirling, E. B. and D. Gottlieb: Methods for characterization of Streptomyces species. International Journal of Systematic Bacteriology, 16, 313–340, 1966
2) Waksman, S. A.: The actinomycetes Vol. 2: Classification, identification and description of genera and species : The Williams and Wilkins Co., Baltimore, 1961
3) Kornerup, A. and J. H. Wanscher: Methuen Handbook of Colour, Methuen, London, 1978
4) Becker, B., M. P. Lechevalier, R. E. Gordon and H. A. Lechevalier: Rapid differentiation between Nocardia and Streptomyces by paper chromatography of whole-cell hydrolysates: Appl. Microbiol. 12, 421–423, 1964
5) Yamaguchi, T.: Comparison of the cell wall composition of morphologically distinct actinomycetes: J. Bacteriol. 89, 444–453, 1965
6) Pridham, T. G. and D. Gottlieb: The utilization of carbon compounds by some Actinomycetales as an aid for species determination: J. Bacteriol. 56: 107–114, 1948
7) Buchanan, R. E. and N. E. Gibbons: Bergey's Manual of Determinative Bacteriology, 8th edition: The Williams and Wilkins Co., Baltimore, 1974
8) Shirling, E. B. and D. Gottlieb: Cooperative description of type culture of Streptomyces. 2. Species descriptions from first study. Intern. J. Syst. Bacteriol. 18: 69–189, 1968
9) Shirling, E. B. and D. Gottlieb: Cooperative description of type culture of Streptomyces. 3. Additional species descriptions from first and second studies. Intern. J. Syst. Bacteriol. 18: 279–392, 1968
10) Shirling, E. B. and D. Gottlieb: Cooperative description of type culture of Streptomyces. 4. Species descriptions from the second, third and forth studies. Intern. J. Syst. Bacteriol. 19: 391–512, 1969
11) Skerman, V. B. D.; V. McGowan & P. H. A. Sneath: Approved list of bacterial names. Intern. J. Syst. Bacteriol. 30: 225–420, 1980
12) Moore, W. E. C., E. P. Cato & L. V. H. Moore: Index of Bacterial and Yeast Nomenclatural Changes Published in the I. J. S. B. Since the 1980 Approved Lists of Bacterial Names. Intern. J. Syst. Bacteriol. 35: 382–407, 1985

WS7622A, B, C and D SUBSTANCES

The WS7622A, B, C and D substances are produced when WS7622A, B, C and D substances-producing strain belonging to the genus Streptomyces is grown in a nutrient medium containing sources of assimilable carbon and nitrogen under aerobic conditions (e.g. shaking culture, submerged culture, etc.). The medium may be either synthetic, semi-synthetic or natural.

Preferred carbon sources may be glucose, mannose, glycerin, molasses, starch, starch hydrolysate and so on, and preferred nitrogen sources may be meat extract, casein hydrolysate, peptone, gluten meal, corn meal, cottonseed meal, soybean meal, corn steep liquor, dried yeast, ammonium phosphate, ammonium sulfate, urea and so on. There may also be incorporated inorganic salts such as the phosphates, chlorides and other salts of metals, e.g. disodium hydrogen phosphate, potassium dihydrogen phosphate, calcium carbonate, ferrous sulfate magnesium sulfate, copper sulfate, zinc sulfate, manganese chloride, magnesium chloride, etc. If copious foaming is encountered during fermentation, a deforming agent such as vegetable oils, e.g. soybean oil, linseed oil, etc., higher alcohols, e.g. octadecanol, may be added in suitable amounts.

The fermentation is preferably conducted at around 30° C. for 50 to 200 hours.

From the above-mentioned fermentation conditions, the optimum set of conditions is selected according to the characteristics of the strain of microorganism employed.

Since a major portion of the WS7622A, B, C and D substances thus produced in the culture broth is present intracellularly, the cultured broth is first filtered. To the mycelial cake obtained there is added a suitable solvent such as acetone and the desired compound is then separated and purified from the resultant mixture by the procedure employed commonly in the production of antibiotics in general. For example, there may be employed such procedures as concentration under reduced pressure, freeze drying, solvent extraction, pH adjustment, treatment with an anion exchange resin, cation exchange resin, nonionic adsorbent resin, etc., treatment with an adsorbent agent such as activated carbon, silicic acid, silica gel or alumina, crystallization, and recrystallization, either singly or in an optional combination.

The WS7622 components, A, B, C and D can be separated from the cultured broth, for example, by the following High Performance Liquid Chromatography data:

Column: Yamamura Chemical Institute, Kyoto, A-302 (ODS 6$\phi$×150 mm)
Mobile phase: $CH_3OH$—$CH_3CN$—0.3% aq.$H_3PO_4$ (10:1:10)
Detection: 210 nm
Flow rate: 1 ml/min
Retention Time (min):
 WS7622A: 6.93
 WS7622B: 10.08
 WS7622C: 5.30
 WS7622D: 4.38

The WS7622A, B, C and D substances produced in the culture broth can be isolated in its free form or if desired, in the form of a pharmaceutically acceptable salt, respectively. For isolating these substances in the form of a pharmaceutically acceptable salt, the desired compound obtained from the mycelial extract is treated with a base such as an inorganic base, e.g. an alkali metal compound (e.g. sodium hydroxide, potassium hydroxide, etc.), an alkaline earth metal compound (e.g. calcium hydroxide, magnesium hydroxide, etc.), an inorganic base, e.g. ammonia, etc., an organic base (e.g. triethylamine, dicyclohexylamine, etc.) or an acid such as an inorganic acid (e.g. hydrochloric acid, sulfuric acid, phosphoric acid, etc.) or an organic acid (e.g. formic acid, acetic acid, p-toluenesulfonic acid, citric acid, oxalic acid, etc.), whereby each of the corresponding salt of WS7622A, B, C and D substances can be obtained.

Each of the salt of WS7622A, B, C and D substances thus obtained can be reconverted to free WS7622A, B, C and D substances in the per se conventional manner.

(1) WS7622A SUBSTANCE

The WS7622A substance is a new substance and has the following physico-chemical properties.

Physico-chemical properties of WS7622A substance:
Appearance: Colorless prism
Nature of substance: acidic
Color reaction:
 positive; cerium sulfate, iodine vapor
 negative; ninhydrin, Molish
Solubility:
 soluble; methanol, ethanol, n-butanol
 sparingly soluble; chloroform, acetone, ethyl acetate
 insoluble; water, n-hexane
Thin Layer Chromatography (TLC):
 chloroform-methanol (5:1, v/v): Rf 0.51
 acetone-methanol (10:1): 0.62
 (Kiesel gel 60 F254 silica gel plate, Merck)
Melting point: 250°-252° C. (dec.)
Specific rotation: $[\alpha]_D^{23} +36°$ (c=1.0, MeOH)

| UV spectrum: | $\gamma_{max}^{MeOH}$ | 287 nm ($\epsilon$ = 3600) |
|---|---|---|
| | $\gamma_{max}^{MeOH-HCl}$ | 287 nm |
| | $\gamma_{max}^{MeOH-NaOH}$ | 298 nm |

Molecular formula: $C_{47}H_{63}N_9O_{13}$
Elemental analysis: Calcd. ($C_{47}H_{63}N_9O_{13}\cdot 2H_2O$); C 56.56, H 6.77, N 12.63%. Found; C 56.65, H 6.62, N 12.27%.
Molecular weight: FAB-MS m/z 984 (M+Na)+
Infrared absorption spectrum (attached FIG. 1):
$\nu_{max}^{KBr}$ 3400, 3300, 3060, 2980, 2940, 1735, 1710, 1690, 1670, 1660, 1640, 1540, 1520, 1470, 1380, 1330, 1300, 1260, 1220, 1200, 1160, 1130, 1090, 1000, 980, 940, 920 cm$^{-1}$

Figure 2:
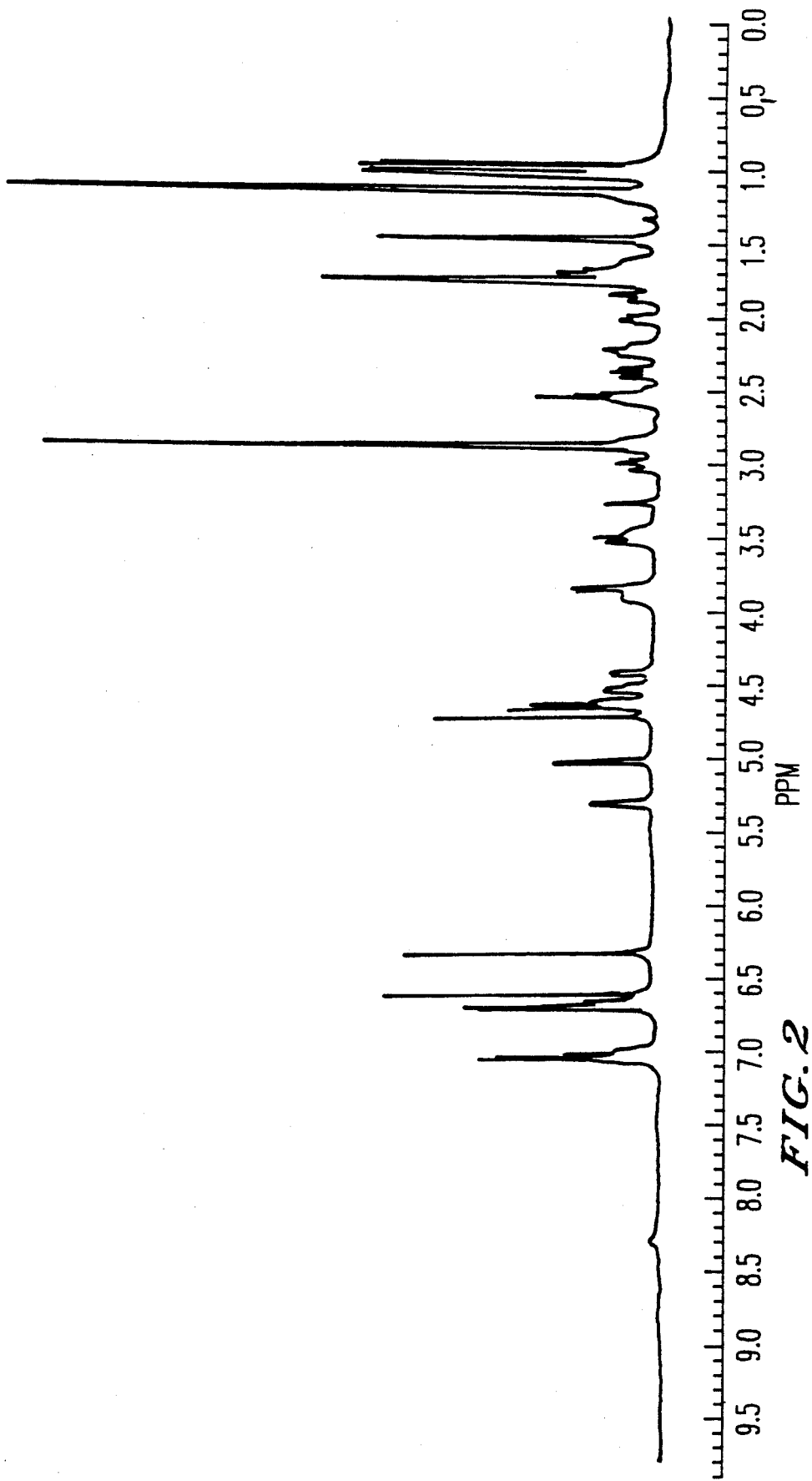
FIG. 2 is an NMR spectrum of WS7622A.

| 1H Nuclear magnetic resonance spectrum (attached FIG. 2): (400 MHz, CD$_3$OD) $\delta$ ||
|---|---|
| 7.22-7.09 | (3H, m) |
| 6.88-6.77 | (3H, m) |
| 6.74 | (1H, s) |
| 6.46 | (1H, s) |
| 5.46 | (1H, m) |
| 5.18 | (1H, s) |
| 4.85 | (1H, s) |
| 4.77 | (1H, m) |
| 4.65 | (1H, m) |
| 4.50 | (1H, m) |
| 3.96 | (1H, m) |
| 3.91 | (1H, d, J=9Hz) |
| 3.60-3.47 | (2H, m) |
| 3.03 | (1H, m) |
| 2.90 | (3H, s) |
| 2.86 | (1H, m) |
| 2.59-2.49 | (2H, m) |
| 2.39 | (1H, m) |
| 2.29-2.16 | (2H, m) |
| 2.00 | (1H, m) |
| 1.84 | (1H, m) |
| 1.74 | (3H, d, J=6Hz) |
| 1.72-1.53 | (4H, m) |
| 1.44 | (3H, d, J=6Hz) |
| 1.12 | (1H, m) |
| 1.10 | (6H, d, J=6Hz) |
| 0.99 | (3H, d, J=6Hz) |

-continued

| $^1$H Nuclear magnetic resonance spectrum (attached FIG. 2): (400 MHz, CD$_3$OD) δ ||
|---|---|
| 0.94 | (3H, d, J=6Hz) |

Figure 3:
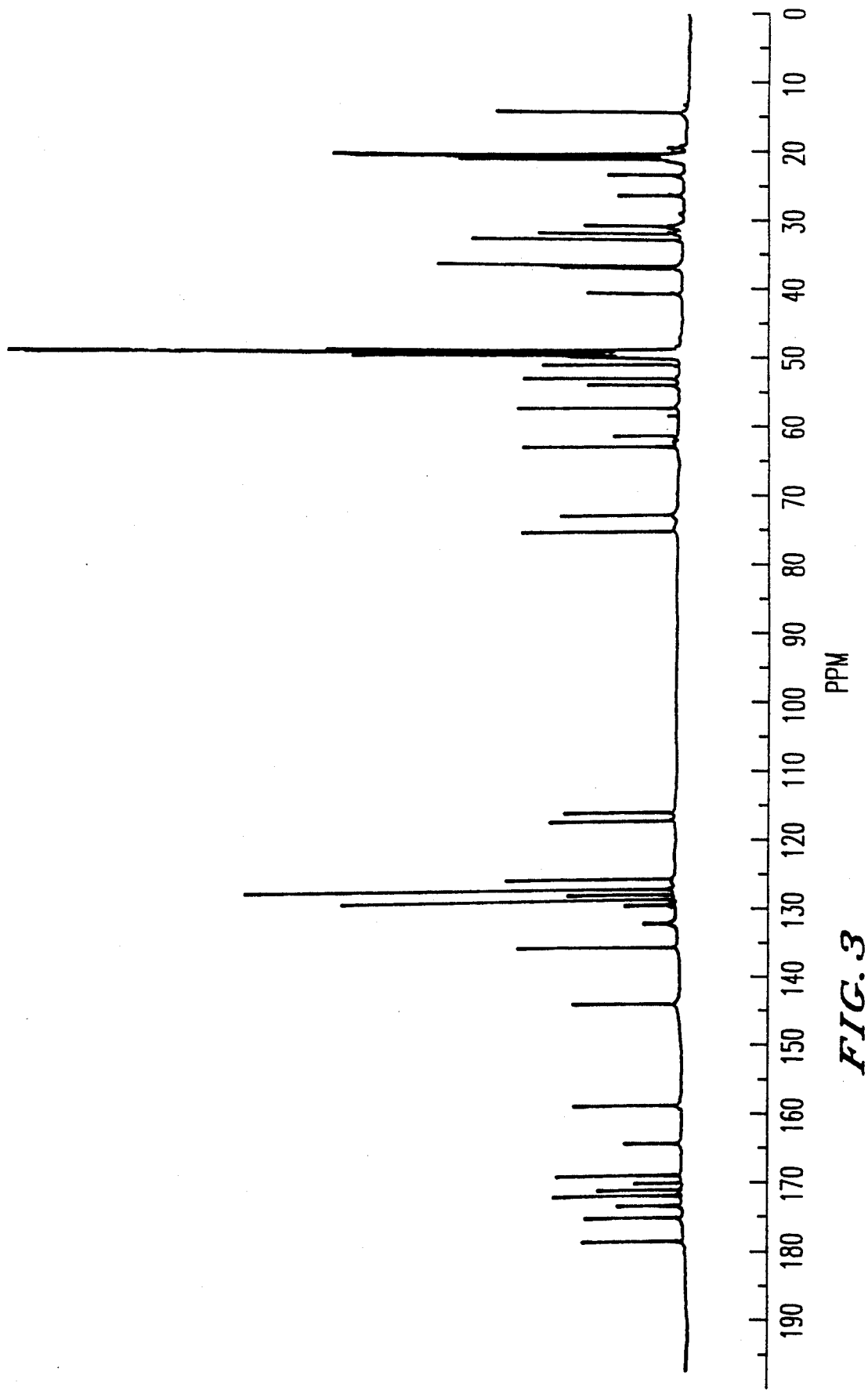
FIG. 3 is a $^{13}C$ NMR spectrum of WS7622A.

| $^{13}$C Nuclear magnetic resonance spectrum (attached FIG. 3): (100 MHz, CD$_3$OD) δ ||
|---|---|
| 179.7 | (s) |
| 176.3 | (s) |
| 174.7 | (s) |
| 173.3 | (s) |
| 172.4 | (s) |
| 171.4 | (s) |
| 170.3 | (s) |
| 165.8 | (s) |
| 160.2 | (s) |
| 145.7 | (s) |
| 145.6 | (s) |
| 137.5 | (s) |
| 134.0 | (d) |
| 131.4 | (s) |
| 130.6 | (d) × 2 |
| 129.8 | (s) |
| 129.1 | (d) × 2 |
| 129.1 | (s) |
| 127.6 | (d) |
| 119.1 | (d) |
| 118.0 | (d) |
| 76.0 | (d) |
| 73.4 | (d) |
| 63.1 | (d) |
| 61.4 | (d) |
| 57.1 | (d) |
| 53.6 | (d) |
| 52.7 | (d) |
| 50.5 | (d) |
| 39.9 | (t) |
| 36.1 | (t) |
| 35.8 | (d) |
| 31.8 | (q) |
| 31.0 | (t) |
| 30.8 | (d) |
| 29.9 | (t) |
| 29.7 | (t) |
| 25.2 | (t) |
| 22.3 | (t) |
| 20.2 | (q) |
| 20.0 | (q) × 2 |
| 19.7 | (q) |
| 19.5 | (q) |
| 13.3 | (q) |

(2) WS7622B SUBSTANCE

The WS7622B substance is a new substance and has the following physico-chemical properties.

Physico-chemical properties of WS7622B substance:

Appearance: Colorless needles

Nature of substance: acidic

Color reaction:
 positive; Cerium sulfate, iodine vapor, ferric chloride
 negative; ninhydrin, Molish, Dragendorff Solubility:
 soluble; methanol, ethanol, n-butanol
 sparingly soluble; chloroform, acetone
 insoluble; water, n-hexane Thin Layer Chromatography (TLC):
 chloroform-methanol (5:1, V/V): Rf 0.55
 (Kiesel gel 60 F254 silica gel plate, Merck)

Melting point: 248°–250° C. (dec.)

Specific rotation: $[\alpha]_D^{23}$ +39° (C=1.0, MeOH)

| UV Spectrum: | | |
|---|---|---|
| $\gamma_{max}^{MeOH}$ | 287 nm (ε = 3800) | |
| $\gamma_{max}^{MeOH-HCl}$ | 287 nm | |
| $\gamma_{max}^{MeOH-NaOH}$ | 299 nm | |

Molecular formula: C$_{48}$H$_{65}$N$_9$O$_{13}$

Elemental analysis: Calcd. (C$_{48}$H$_{65}$N$_9$O$_{13}$.3H$_2$O); C 55.96, H 6.95, N 12.24%. Found; C 55.84, H 7.05, N 12.12%.

Molecular weight: FAB-MS m/z 998 (M+Na)$^+$

Figure 4:
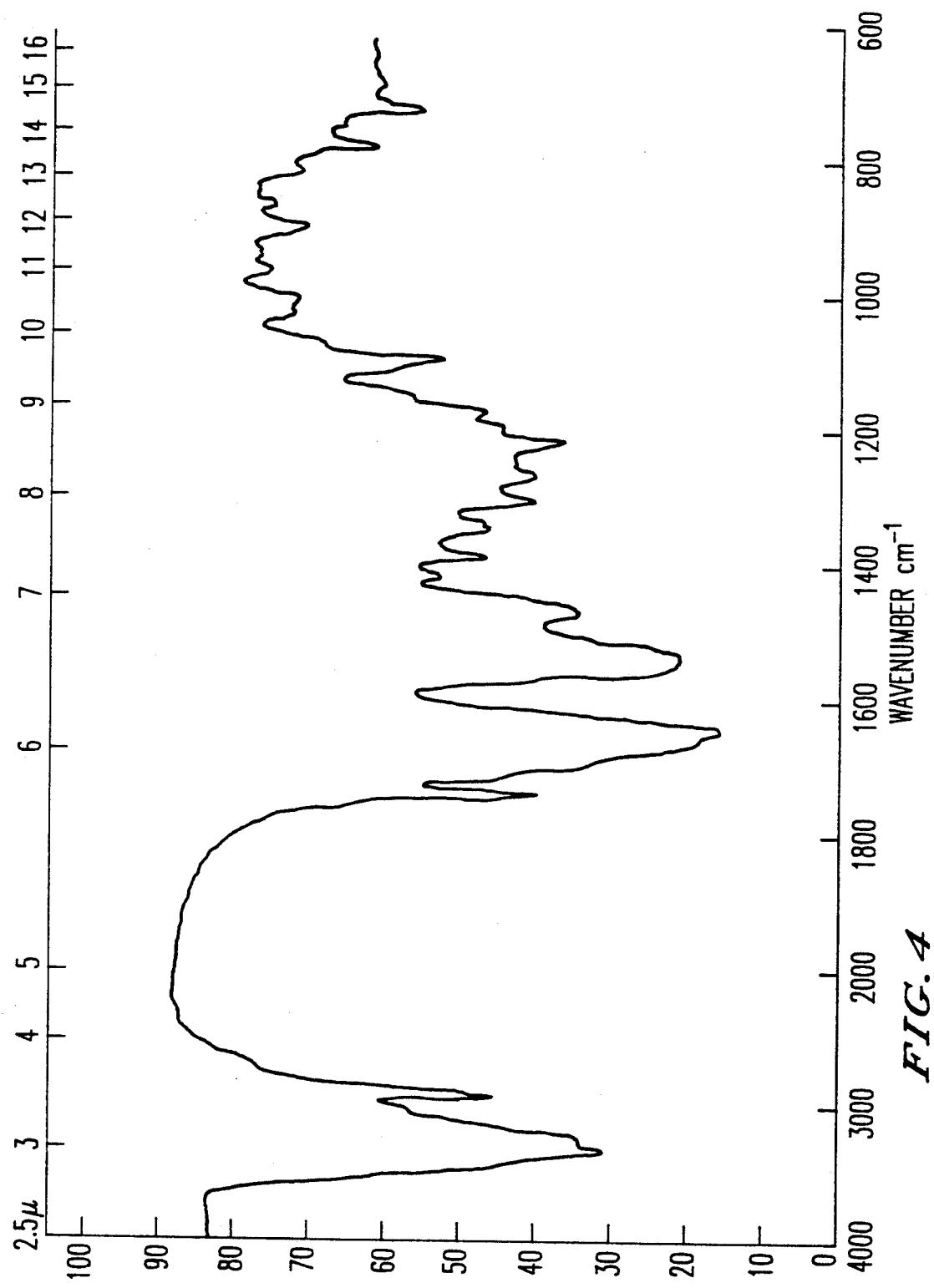
FIG. 4 is an infrared absorption spectrum of WS7622B.

Infrared absorption spectrum (attached FIG. 4): $\nu_{max}^{KBr}$ 3400, 3300, 2960, 1735, 1680, 1660, 1640, 1540, 1520, 1460, 1400, 1380, 1330, 1290, 1250, 1200, 1180, 1150, 1130, 1080, 1050, 1000, 980, 940, 920 cm$^{-1}$

Figure 5:
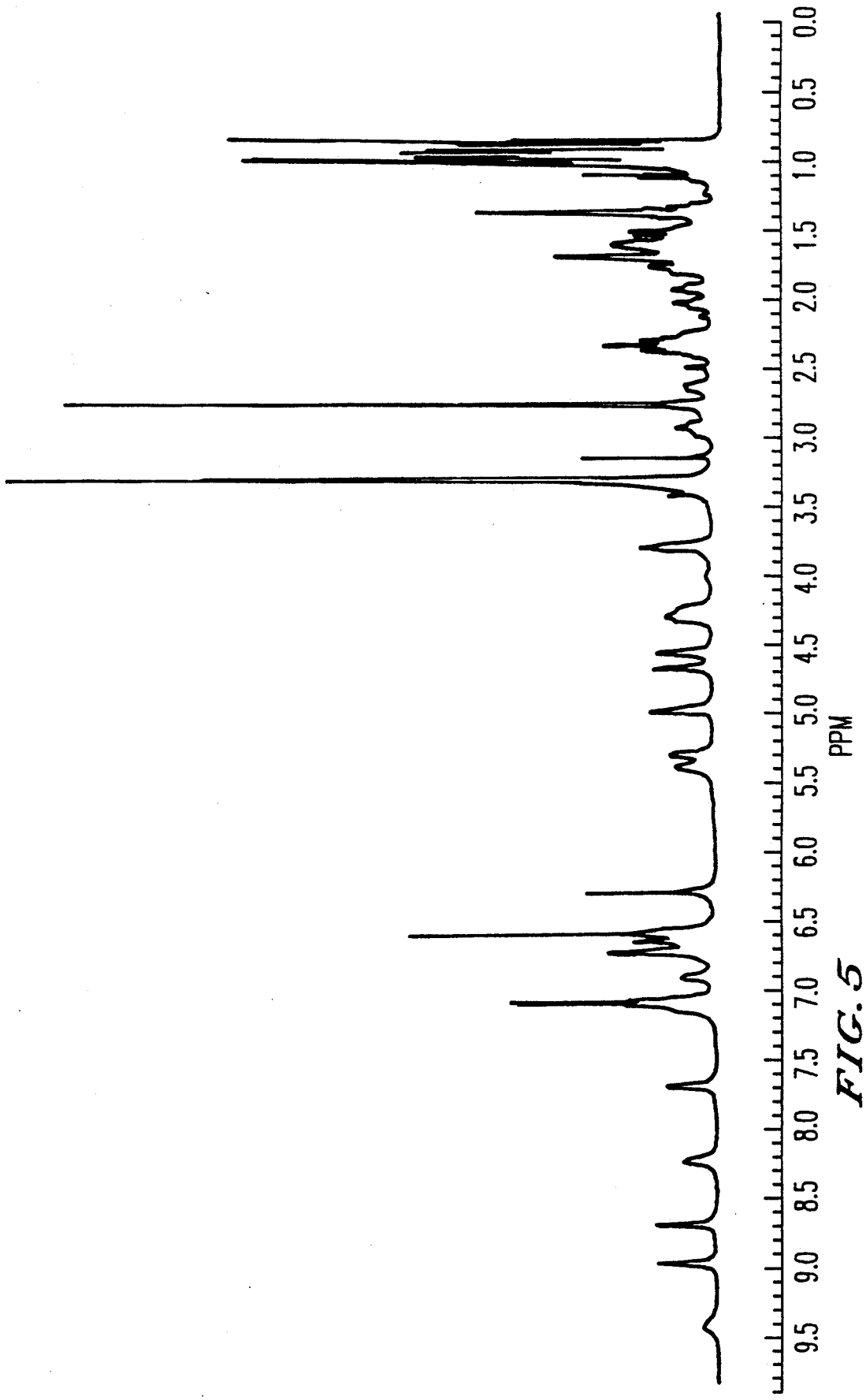
FIG. 5 is an NMR spectrum of WS7622B.

| $^1$H Nuclear magnetic resonance spectrum (attached FIG. 5): (400 MHz, DMSO-d$_6$) δ ||
|---|---|
| 9.48 | (1H, broad s) |
| 9.03 | (1H, broad s) |
| 8.76 | (1H, broad s) |
| 8.30 | (1H, broad d, J=6Hz) |
| 7.77 | (1H, d, J=7Hz) |
| 7.21 | (1H, d, J=8Hz) |
| 7.20–7.11 | (3H, m) |
| 6.97 | (1H, broad d, J=7Hz) |
| 6.80 | (2H, d, J=8Hz) |
| 6.72 | (1H, broad s) |
| 6.67 | (1H, s) |
| 6.63 | (1H, q, J=7Hz) |
| 6.37 | (1H, s) |
| 5.48 | (1H, m) |
| 5.40 | (1H, m) |
| 5.09 | (1H, m) |
| 4.77 | (1H, m) |
| 4.64 | (1H, m) |
| 4.38 | (1H, m) |
| 4.31 | (1H, m) |
| 3.87–3.80 | (2H, m) |
| 3.40–3.30 | (2H, m) |
| 2.95 | (1H, m) |
| 2.79 | (3H, s) |
| 2.65 | (1H, m) |
| 2.40–2.20 | (4H, m) |
| 2.00 | (1H, m) |
| 1.87 | (1H, m) |
| 1.73 | (1H, m) |
| 1.65 | (3H, d, J=7Hz) |
| 1.65–1.40 | (5H, m) |
| 1.32 | (3H, d, J=6Hz) |
| 1.27 | (1H, m) |
| 0.97 | (3H, d, J=6Hz) |
| 0.97 | (1H, m) |
| 0.91 | (3H, d, J=6Hz) |
| 0.88 | (3H, d, J=6Hz) |
| 0.81 | (3H, t, J=7Hz) |

Figure 6:
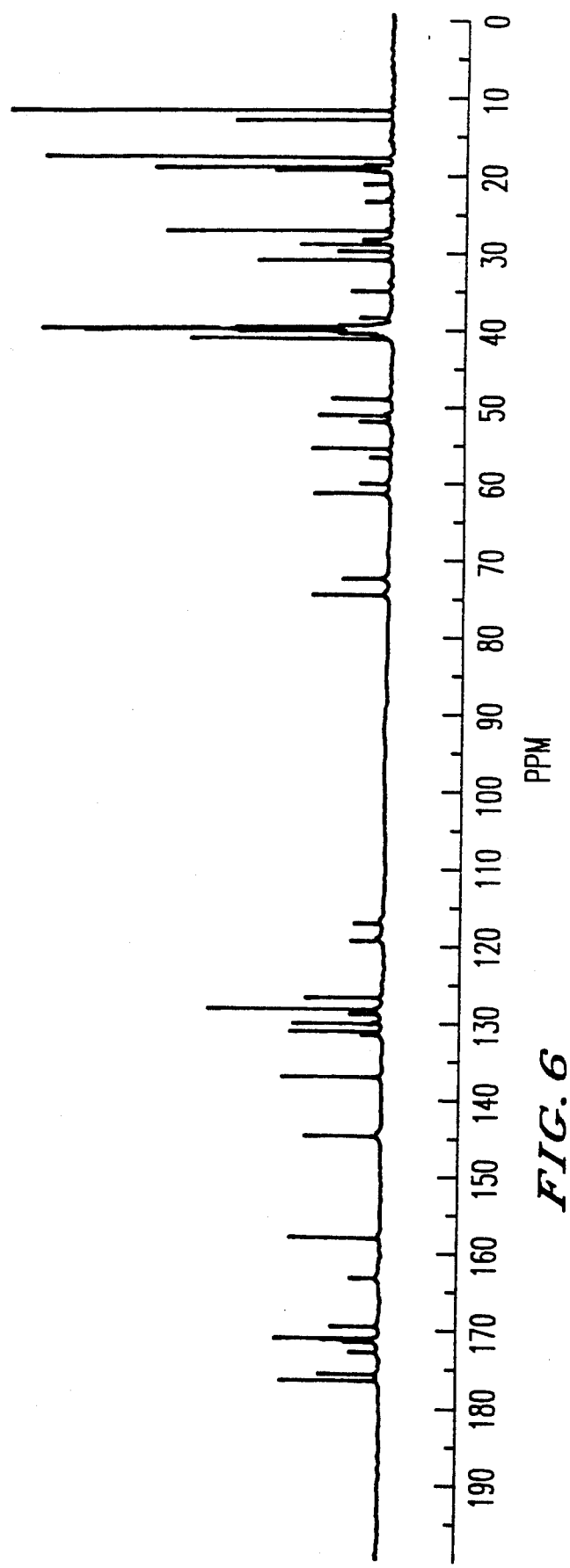
FIG. 6 is a $^{13}C$ NMR spectrum of WS7622B.

| $^{13}$C Nuclear magnetic resonance spectrum (attached FIG. 6): (100 MHz, DMSO-d$_6$) δ ||
|---|---|
| 175.6 | (s) |
| 174.8 | (s) |
| 172.0 | (s) |
| 170.9 | (s) |
| 170.6 | (s) |
| 170.3 | (s) |
| 168.7 | (s) |
| 162.5 | (s) |
| 157.4 | (s) |
| 144.2 | (s) |
| 144.2 | (s) |
| 136.5 | (s) |
| 131.1 | (d) |
| 130.7 | (s) |
| 129.6 | (d) × 2 |
| 128.4 | (s) |
| 127.9 | (d) × 2 |

| 13C Nuclear magnetic resonance spectrum (attached FIG. 6): (100 MHz, DMSO-d₆) δ | |
|---|---|
| 127.8 | (s) |
| 126.4 | (d) |
| 118.9 | (d) |
| 116.8 | (d) |
| 74.2 | (d) |
| 72.1 | (d) |
| 61.0 | (d) |
| 59.8 | (d) |
| 55.2 | (d) |
| 51.6 | (d) |
| 50.8 | (d) |
| 48.6 | (d) |
| 40.9 | (d) |
| 38.2 | (t) |
| 35.0 | (t) |
| 30.8 | (q) |
| 29.8 | (t) |
| 28.8 | (d) |
| 28.4 | (t) |
| 28.1 | (t) |
| 27.1 | (t) |
| 23.3 | (t) |
| 21.2 | (t) |
| 19.6 | (q) |
| 19.1 | (q) |
| 19.0 | (q) |
| 17.7 | (q) |
| 12.9 | (q) |
| 11.9 | (q) |

(3) WS7622C SUBSTANCE

The WS7622C substance is a new substance and has the following physico-chemical properties.

Physico-chemical properties of WS7622C substance:
Appearance: Colorless needles
Nature of substance: acidic
Color reaction:
  positive; Cerium sulfate, iodine vapor, ferric chloride
  negative; ninhydrin, Molish, Dragendorff
Solubility:
  soluble; methanol, ethanol
  sparingly soluble; chloroform, acetone, ethyl acetate
  insoluble; water, n-hexane
Thin Layer Chromatography (TLC):
  chloroform-methanol (4:1, V/V): Rf 0.56
  (Kiesel gel 60 F254 silica gel plate, Merck)
Melting point: 250°–252° C. (dec.)
Specific rotation: $[\alpha]_D^{23} +36°$ (C=0.5, MeOH)

| UV spectrum: | $\gamma_{max}^{MeOH}$ | 287 nm ($\epsilon$ = 3500) |
|---|---|---|
| | $\gamma_{max}^{MeOH-HCl}$ | 287 nm |
| | $\gamma_{max}^{MeOH-NaOH}$ | 298 nm |

Figure 7:
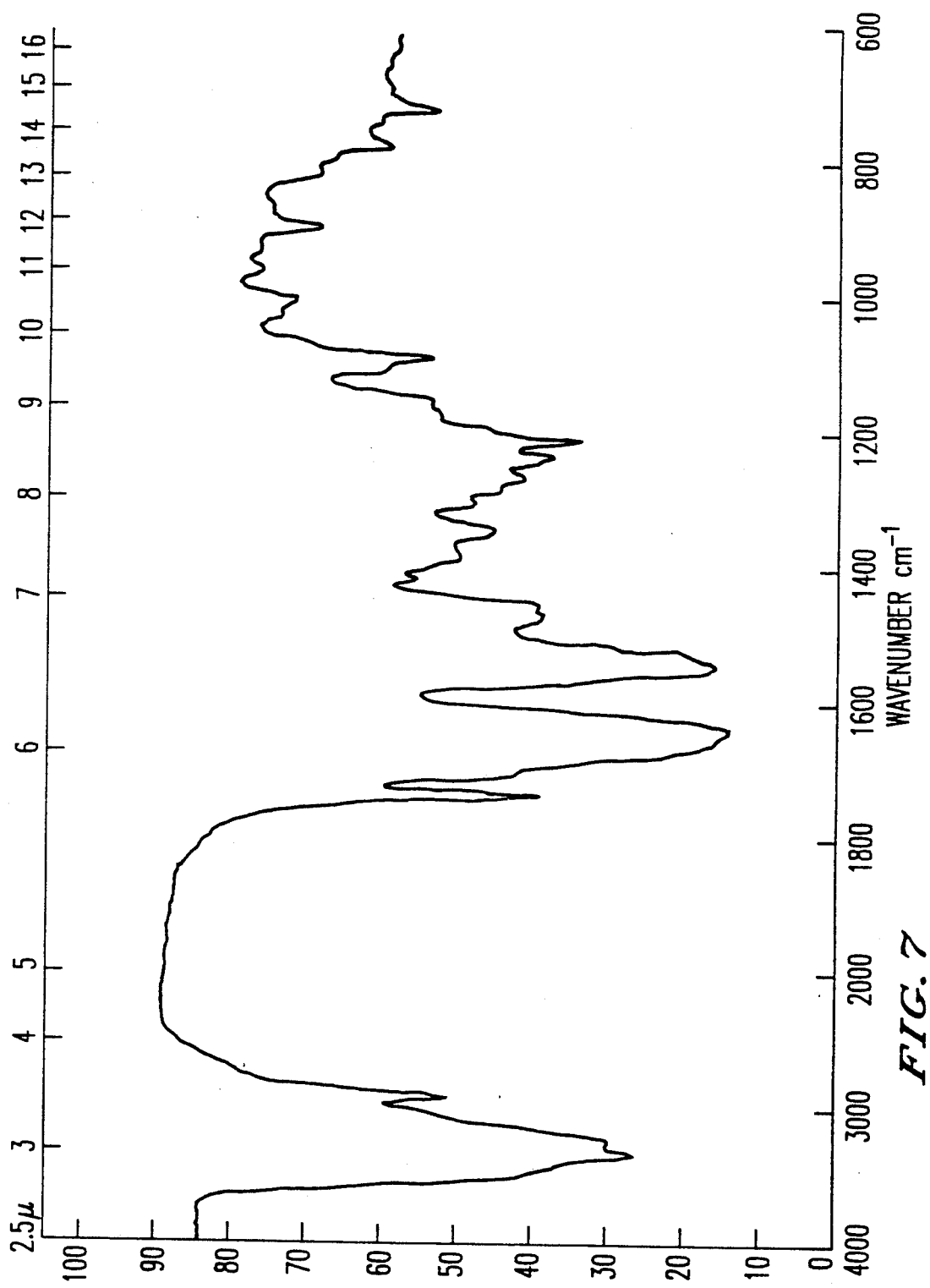
FIG. 7 is an infrared absorption spectrum of WS7622C.

Molecular formula: $C_{46}H_{61}N_9O_{13}$
Elemental analysis: Calcd. ($C_{46}H_{61}N_9O_{13}\cdot 6H_2O$); C 52.31, H 6.97, N 11.94%. Found; C 51.95, H 6.66, N 11.77%.
Molecular weight: FAB-MS m/z 970 (M+Na)⁺
Infrared absorption spectrum (attached FIG. 7): $\nu_{max}^{KBr}$ 3400, 3300, 2980, 1740, 1700, 1660, 1640, 1540, 1470, 1450, 1410, 1335, 1260, 1230, 1200, 1160, 1140, 1070, 1010, 980, 940, 920, 880 cm⁻¹

Figure 8:
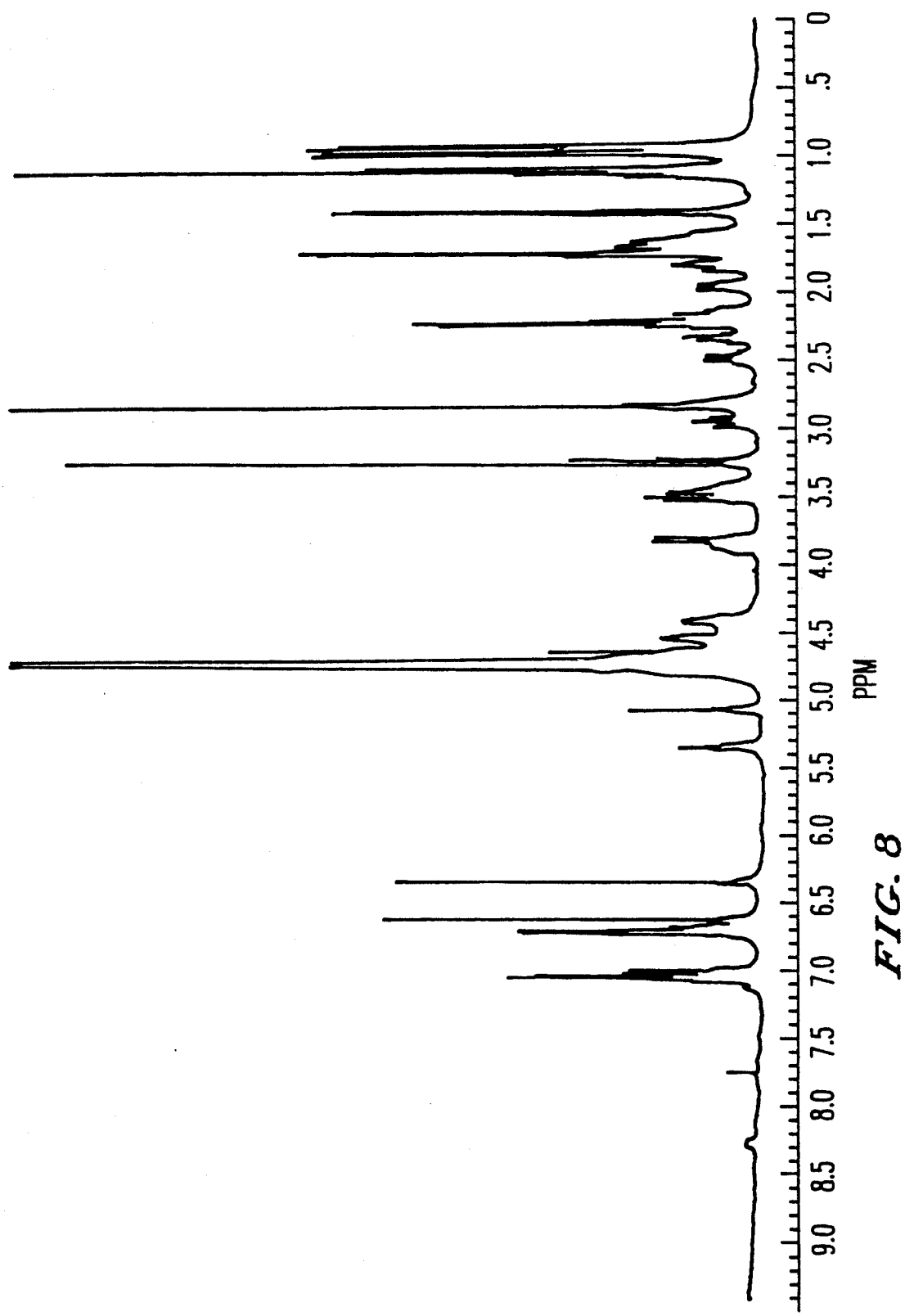
FIG. 8 is an NMR spectrum of WS7622C.

| ¹H Nuclear magnetic resonance spectrum (attached FIG. 8): (400 MHz, CD₃OD) δ | |
|---|---|
| 7.21–7.10 | (3H, m) |
| 6.86–6.77 | (3H, m) |
| 6.75 | (1H, s) |
| 6.47 | (1H, s) |
| 5.46 | (1H, m) |
| 5.18 | (1H, m) |
| 4.85 | (1H, s) |
| 4.74 | (1H, m) |
| 4.65 | (1H, m) |
| 4.51 | (1H, m) |
| 3.94 | (1H, m) |
| 3.90 | (1H, d, J=10Hz) |
| 3.58–3.46 | (2H, m) |
| 3.02 | (1H, m) |
| 2.90 | (3H, s) |
| 2.86 | (1H, m) |
| 2.55 | (1H, m) |
| 2.38 | (1H, dd, J=14 and 11Hz) |
| 2.28 | (2H, q, J=7Hz) |
| 2.30–2.16 | (2H, m) |
| 1.99 | (1H, m) |
| 1.84 | (1H, m) |
| 1.75 | (3H, d, J=7Hz) |
| 1.78–1.54 | (4H, m) |
| 1.44 | (3H, d, J=6.5Hz) |
| 1.13 | (3H, t, J=7Hz) |
| 1.12 | (1H, m) |
| 1.01 | (3H, d, J=6.5Hz) |
| 0.97 | (3H, d, J=6.5Hz) |

Figure 9:
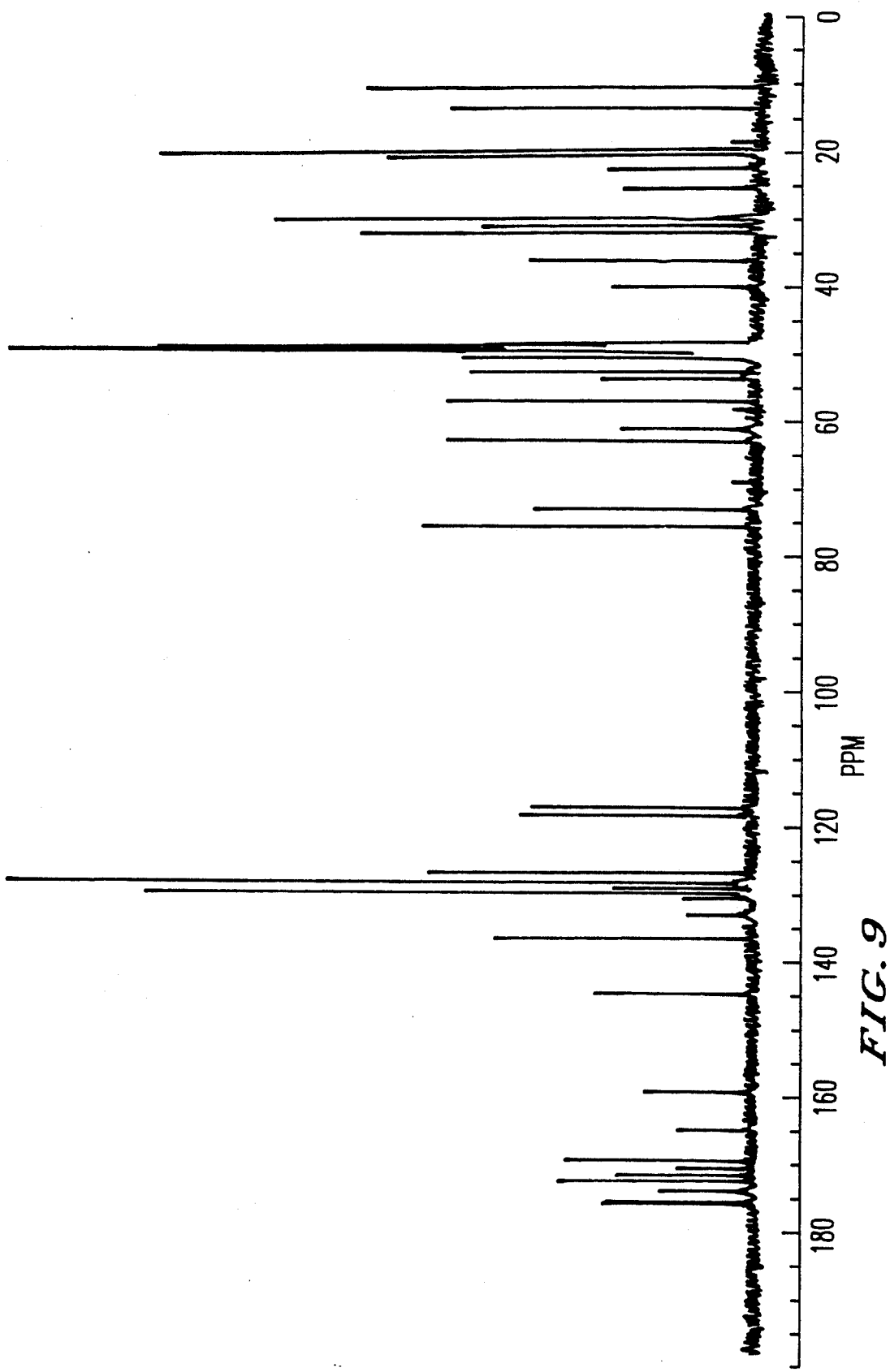
FIG. 9 is a $^{13}C$ NMR spectrum of WS7622C.

| ¹³C Nuclear magnetic resonance spectrum (attached FIG. 9): (100 MHz, CD₃OD) δ | |
|---|---|
| 176.7 | (s) |
| 176.4 | (s) |
| 174.7 | (s) |
| 173.4 | (s) |
| 172.5 | (s) |
| 171.4 | (s) |
| 170.4 | (s) |
| 165.8 | (s) |
| 160.4 | (s) |
| 145.8 | (s) |
| 145.7 | (s) |
| 137.5 | (s) |
| 134.0 | (d) |
| 131.4 | (s) |
| 130.6 | (d) × 2 |
| 129.8 | (s) |
| 129.1 | (d) × 2 |
| 129.1 | (s) |
| 127.7 | (d) |
| 119.1 | (d) |
| 118.0 | (d) |
| 76.0 | (d) |
| 73.5 | (d) |
| 63.1 | (d) |
| 61.4 | (d) |
| 57.1 | (d) |
| 53.7 | (d) |
| 52.7 | (d) |
| 50.5 | (d) |
| 39.9 | (t) |
| 36.1 | (t) |
| 31.8 | (q) |
| 31.0 | (t) |
| 30.8 | (d) |
| 29.9 | (t) |
| 29.7 | (t) |
| 29.7 | (t) |
| 25.3 | (t) |
| 22.3 | (t) |
| 20.2 | (q) |
| 19.4 | (q) |
| 19.4 | (q) |
| 13.3 | (q) |

-continued

| 13C Nuclear magnetic resonance spectrum (attached FIG. 9): (100 MHz, CD3OD) δ | |
|---|---|
| 10.3 | (q) |

(4) WS7622D SUBSTANCE

The WS7622D substance is a new substance and has the following physico-chemical properties.
Physico-chemical properties of WS7622D substance:
Appearance: Colorless needles
Nature of substance: acidic
Color reaction:
  positive; Cerium sulfate, iodide vapor, ferric chloride
  negative; ninhydrin, Molish, Dragendorff
Solubility:
  Soluble; methanol, ethanol
  sparingly soluble; water, chloroform
  insoluble; n-hexane
Thin Layer Chromatography (TLC):
  chloroform-methanol (4:1, V/V): Rf 0.45
  (Kiesel gel 60 F254 silica gel plate, Merck)
Melting point: 250°–252° C. (dec.)
Specific rotation: $[\alpha]_D^{24} + 35.8°$ (C=0.5, MeOH)

| UV spectrum: | $\gamma_{max}^{MeOH}$ | 287 nm ($\epsilon$ = 3640) |
|---|---|---|
| | $\gamma_{max}^{MeOH-HCl}$ | 287 nm |
| | $\gamma_{max}^{MeOH-NaOH}$ | 298 nm |

Figure 10:
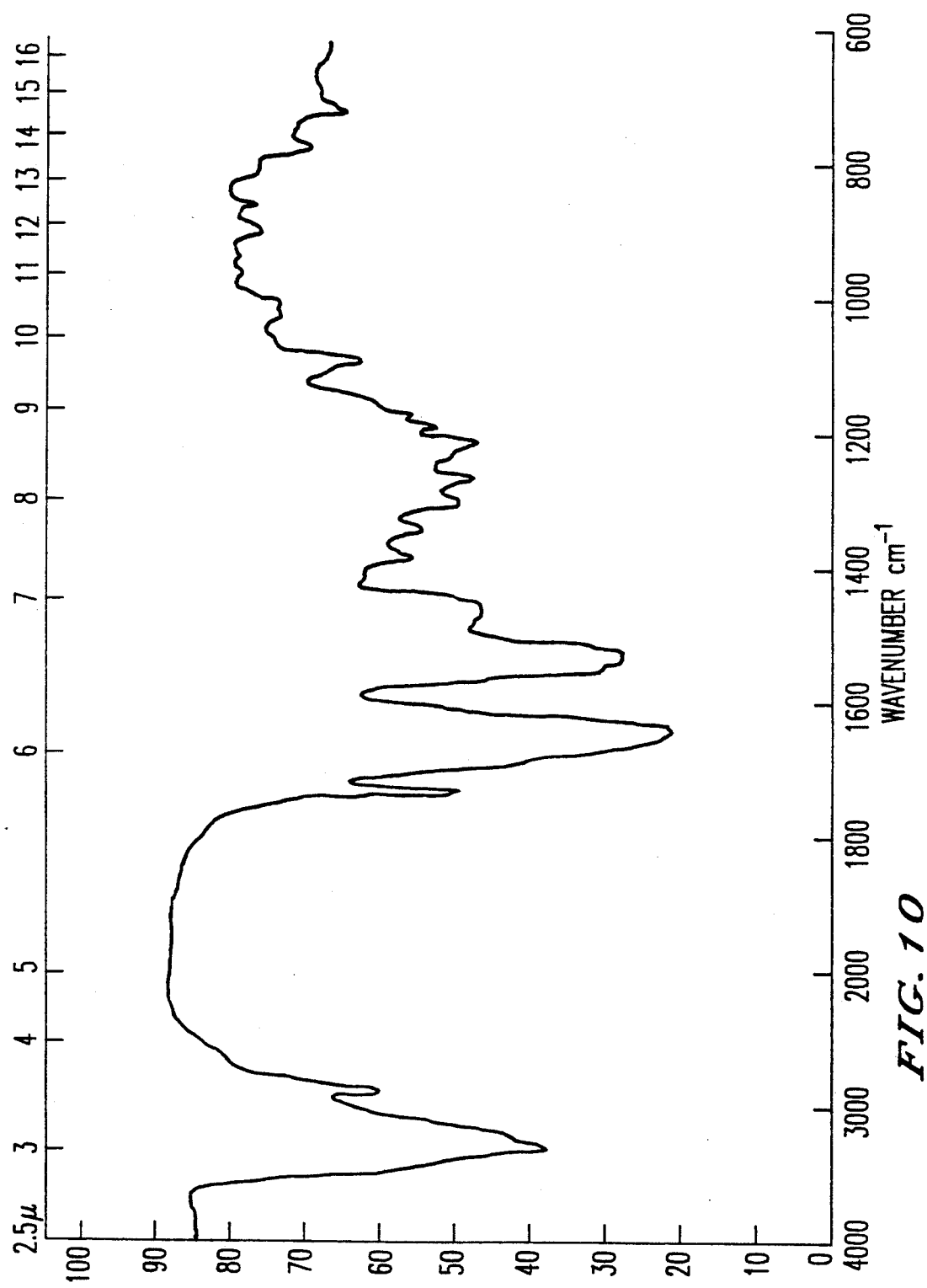
FIG. 10 is an infrared absorption spectrum of WS7622D.

Molecular formula: $C_{45}H_{59}N_9O_{13}$
Elemental analysis: Calcd. ($C_{45}H_{59}N_9O_{13} \cdot 6H_2O$); C 51.86, H 6.87, N 12.10%. Found; C 51.90, H 6.26, N 12.08%.
Molecular weight: FAB-MS m/z 956 (M+Na)+
Infrared absorption spectrum (attached FIG. 10):
$\nu_{max}^{KBr}$ 3360, 2950, 1730, 1700, 1680, 1660, 1640, 1530, 1460, 1380, 1330, 1290, 1250, 1200, 1170, 1160, 1140, 1080, 980, 940, 920, 880 cm$^{-1}$

Figure 11:
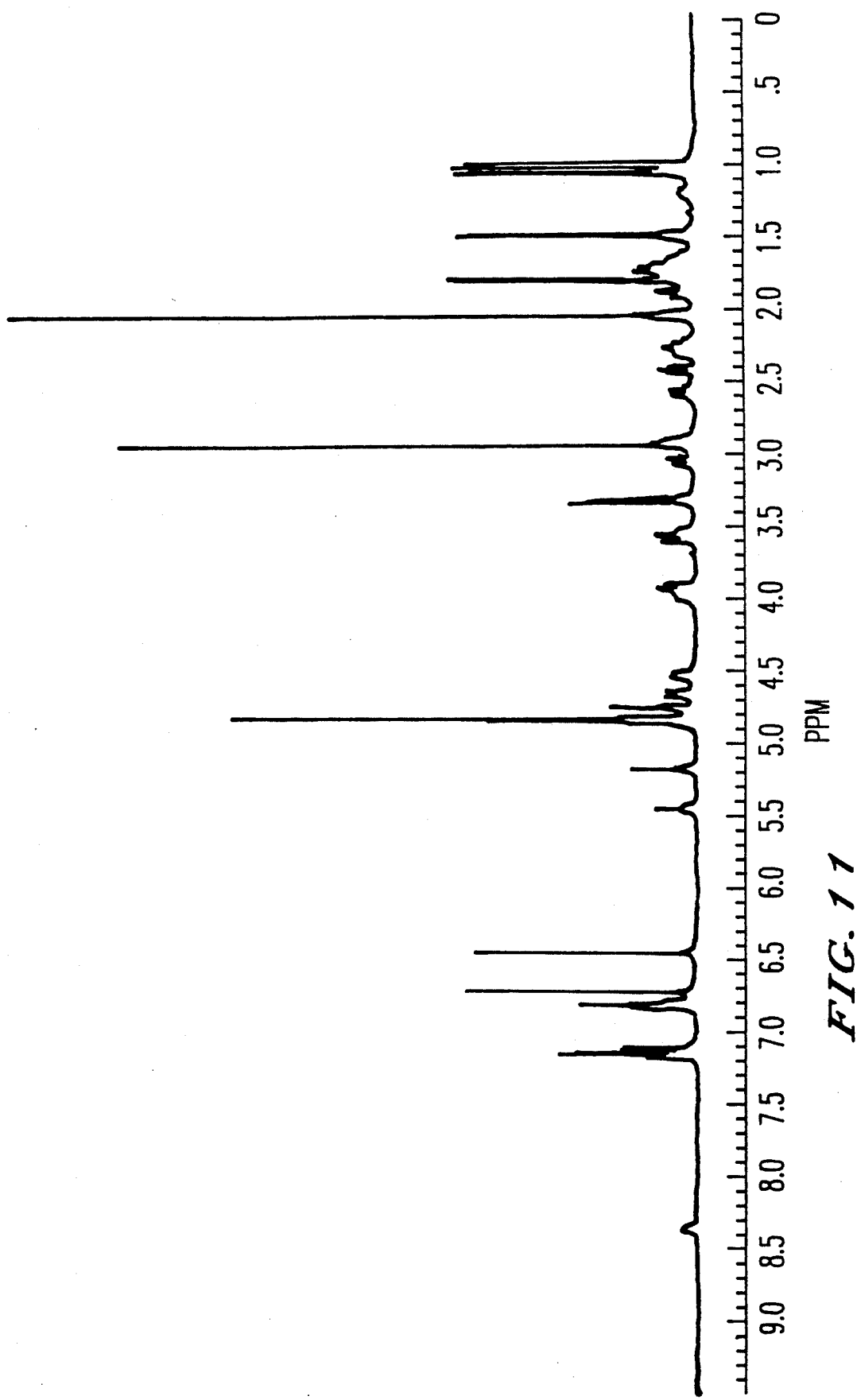
FIG. 11 is an NMR spectrum of WS7622D.

| 1H Nuclear magnetic resonance spectrum (attached FIG. 11): (400 MHz, CD3OD) δ | |
|---|---|
| 7.20–7.10 | (3H, m) |
| 6.85–6.77 | (3H, m) |
| 6.73 | (1H, s) |
| 6.46 | (1H, s) |
| 5.46 | (1H, m) |
| 5.18 | (1H, m) |
| 4.84 | (1H, s) |
| 4.73 | (1H, m) |
| 4.64 | (1H, m) |
| 4.50 | (1H, m) |
| 3.99–3.87 | (2H, m) |
| 3.58–3.46 | (2H, m) |
| 3.01 | (1H, m) |
| 2.90 | (3H, s) |
| 2.87 | (1H, m) |
| 2.53 | (1H, m) |
| 2.38 | (1H, dd, J=14 and 11Hz) |
| 2.30–2.16 | (2H, m) |
| 2.00 | (1H, m) |
| 1.99 | (3H, s) |
| 1.84 | (1H, m) |
| 1.75 | (3H, d, J=7Hz) |
| 1.76–1.55 | (4H, m) |
| 1.43 | (3H, d, J=6.5Hz) |
| 1.15 | (1H, m) |
| 1.00 | (3H, d, J=6.5Hz) |
| 0.95 | (3H, d, J=6.5Hz) |

Figure 12:
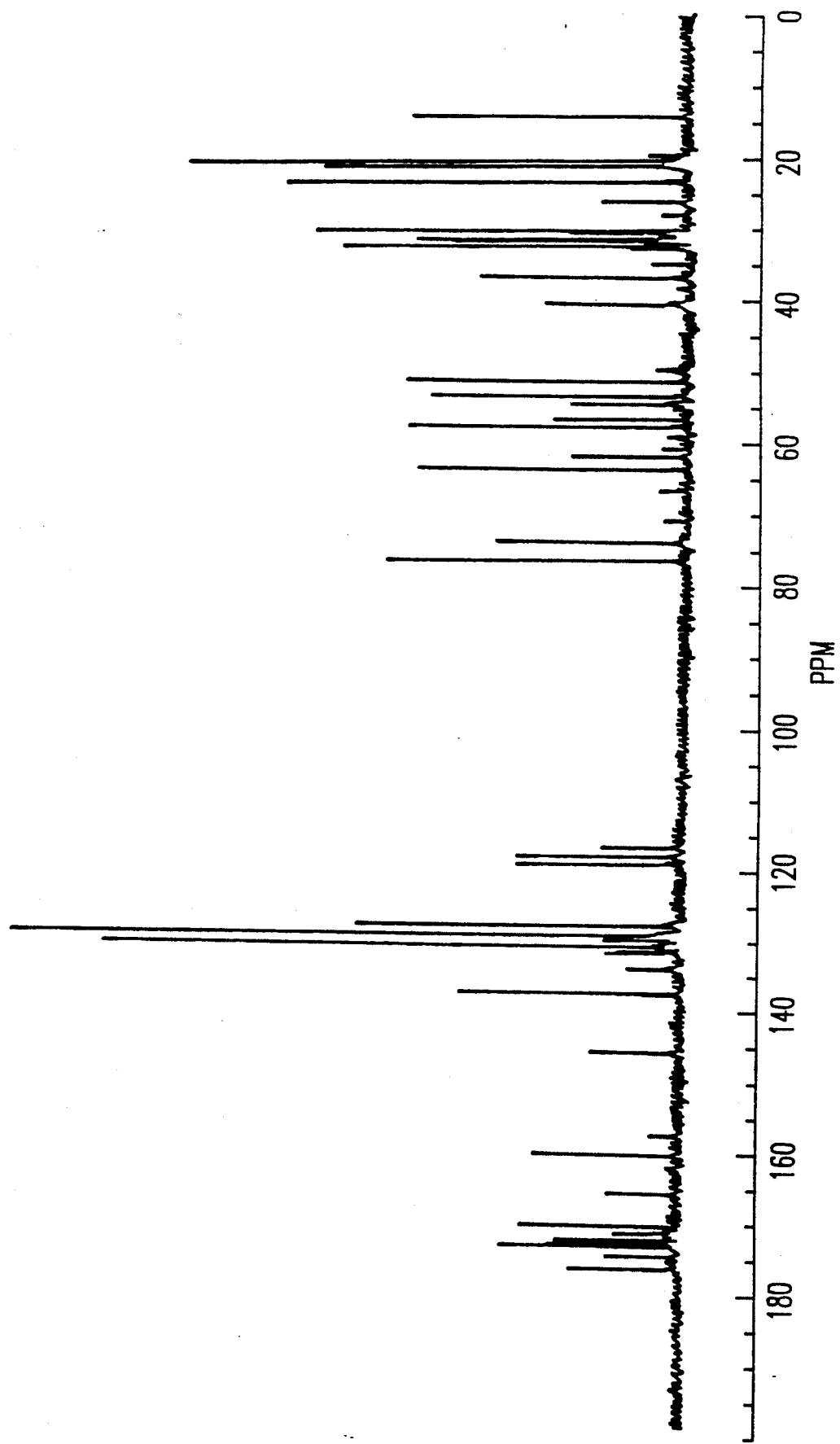
FIG. 12 is a $^{13}C$ NMR spectrum of WS7622D.

| 13C Nuclear magnetic resonance spectrum (attached FIG. 12): (100 MHz, CD3OD) δ | |
|---|---|
| 176.4 | (s) |
| 174.6 | (s) |
| 173.4 | (s) |
| 173.0 | (s) |
| 172.4 | (s) |
| 171.4 | (s) |
| 170.4 | (s) |
| 165.8 | (s) |
| 160.3 | (s) |
| 145.9 | (s) |
| 145.9 | (s) |
| 137.5 | (s) |
| 134.0 | (d) |
| 131.4 | (s) |
| 130.6 | (d) × 2 |
| 129.8 | (s) |
| 129.1 | (d) × 2 |
| 129.1 | (s) |
| 127.6 | (d) |
| 119.0 | (d) |
| 118.0 | (d) |
| 76.0 | (d) |
| 73.5 | (d) |
| 63.1 | (d) |
| 61.3 | (d) |
| 57.1 | (d) |
| 53.9 | (d) |
| 52.7 | (d) |
| 50.5 | (d) |
| 39.9 | (t) |
| 36.1 | (t) |
| 31.8 | (q) |
| 31.0 | (t) |
| 30.7 | (d) |
| 29.9 | (t) |
| 29.6 | (t) |
| 25.3 | (t) |
| 22.4 | (q) |
| 22.3 | (t) |
| 20.2 | (q) |
| 19.5 | (q) |
| 19.4 | (q) |
| 13.3 | (q) |

DERIVATIVES OF WS7622A SUBSTANCE

Derivatives of WS7622A substance of this invention can be represented by the following formula (I):

wherein $R^1$ and $R^2$ are each lower alkyl group or lower alkanoyl group.

A lower alkyl group means one having 1 to 6 carbon atoms, and preferred examples of the lower alkyl group are methyl, ethyl, propyl, isopropyl, butyl, isobutyl, tert-butyl, pentyl or the like.

A lower alkanoyl group means one having 1 to 6 carbon atoms, and preferred examples of the lower alkanoyl are formyl, acetyl, propionyl, butyryl, isobutyryl, valeryl, isovaleryl, pivaloyl, hexanoyl or the like.

Derivatives of WS7622A substance (I) can be prepared by the following methods:

(1) Process 1 (Alkylation of WS7622A substance):

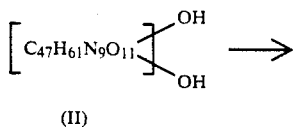

(II)

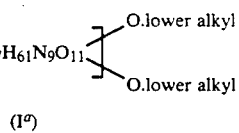

(Iᵃ)

Di-alkylated WS7622A substance (Iᵃ) or its salt can be prepared by reacting the WS7622A substance (II) or its salt with an alkylating agent.

Preferred examples of the salt of compounds (Iᵃ) and (II) may include the same as those exemplified as pharmaceutically acceptable salts of WS7622A, B, C and D substances and derivatives thereof.

Preferred examples of the alkylating agent may include diazoalkanes (e.g. diazomethane, diazoethane, etc.), alkyl halides (e.g. methyl iodide, ethyl iodide, etc.), dialkyl sulfates (e.g. dimethyl sulfate, etc.) and the like.

This reaction is preferably conducted in a solvent inert to the reaction, such as alcohol (e.g. methanol, ethanol, propanol, etc.), chloroform, or a mixture thereof, at ambient temperature.

In some cases, this reaction is preferably carried out in the presence of a conventional base.

(2) Process 2 (Acylation of WS7622A substance):

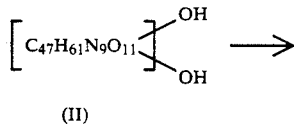

(II)

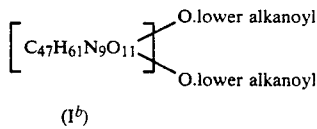

(Iᵇ)

Di-acylated WS7622A substance (Iᵇ) or its salt can be prepared by reacting the WS7622A substance (II) or its salt with a compound of the formula:

R—OH wherein R is lower alkanoyl, or its reactive derivatives.

Preferred examples of salt of the compounds (Iᵇ) and (II) may include the same as those exemplified as pharmaceutically acceptable salts of WS7622A, B, C and D substances and derivatives thereof.

Said reactive derivative may include acid halides, acid azides, acid anhydrides, active amides, active esters and the like.

When a free carboxylic acid (i.e. a compound of the formula: R—OH) is used, this reaction is preferably conducted in the presence of a conventional condensing agent.

This reaction is preferably conducted in a conventional solvent such as alcohol (e.g. methanol, ethanol, propanol, etc.), under ice-cooling or at ambient temperature, and good results are obtained in most cases when this reaction is carried out in the presence of a base such as pyridine. Such a base which is liquid may serve also as solvents.

A pharmaceutically acceptable salt of each of the WS7622A, B, C and D substances and derivatives thereof may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt or the like, and an acid addition salt with organic or inorganic acid such as methane sulfonate, hydrochloride, sulfate, nitrate, phosphate or the like.

The WS7622A, B, C and D substances, derivatives thereof and their pharmaceutical acceptable salt have a human leukocyte elastase-inhibiting activity and is useful as human leukocyte elastase inhibitors for treating degenerative diseases, for example, pulmonary emphysema, atherosclerosis, rheumatoid arthritis, osteoarthritis, psoriasis, pancreatitis, adult respiratory distress syndrome and the like.

In order to illustrate the usefulness of the WS7622A, B, C and D substances, derivatives thereof and their pharmaceutically acceptable salt, pharmacological test data thereof are shown below.

Protease Inhibition Assay (1) Preparation of crude human leukocyte elastase:

Fifty milliliters of blood were obtained from a healthy volunteer. Leukocytes were isolated from the blood by using Mono-Poly resolving medium (FLOW Laboratories, Australia), and were collected by centrifugation. The remaining erythrocytes were lysed by adding distilled water to the precipitate, and centrifuged for 30 min at 3000 rpm. To the resultant precipitate, 10 ml of 2M $NaClO_4$ was added and elastase was extracted. After extraction for 120 min at 0° C., the supernatant containing elastase activity was obtained by centrifugation. After adding an equal volume of chloroform to this supernatant and shaking vigorously, a clear supernatant containing elastase activity was separated. Ten milliliters of the HEPES buffer were added to the supernatant and supplied for the enzyme assay.

(2) Method:

A buffer used throughout the assay was 0.1M HEPES (N-(2-hydroxyethyl)piperazine-N'-2-ethanesulfonic acid) containing 0.5M NaCl, pH 7.5. Twenty-five microliters of 2 mM methoxysuccinyl-(Ala)$_2$-Pro-Val-p-nitroanilide (100 mM of dimethyl sulfoxide solution were diluted in the buffer) and 50 μl of sample (10 μl of sample in organic solvent was diluted 5-fold in the buffer) were mixed in wells of 96 well-microtiter plate. An absorbance of the mixture in wavelength at 415 nm was measured by a microplate reader (Corona Electric Co., Ibaraki, Japan). After the measurement, 25 μl of 6 μg/ml human sputum elastase (HSE) or 25 μl human leukocyte elastase preparation was added and stand for 30 min at room temperature. Then, the absorbance at 415 nm was measured. Percent inhibition by drug was determined by 100×(1-"r" inhibitor present/"r" inhibitor absent), where "r" is absorbance after 30 min incubation minus absorbance before enzyme addition. Effects of inhibitors against other proteases were assayed similarly using N-succinyl-(Ala)$_3$-p-nitroanilide for porcine pancrease elastase (Type IV, 5 μg/ml final), N-alpha-benzoyl-Arg-p-nitroanilide for bovine pancrea trypsin (Type I, 16 μg/ml final), methoxysuccinyl-(Ala)$_2$-Pro-Met-p-nitroanilide for bovine pancreas chymotrypsin (Type II, 1.5 μg/ml final) and for human sputum cathepsin G (10 unit/ml final). HSE and cathepsin G were obtained from Elastin Products Company Inc., MO., U.S.A. All other substrates and proteases were purchased from Sigma Chemicals Co.

(3) Result:

1) Inhibitory effect of WS7622A, B, C and D substances on several serine protease activity

| Substance (µg/ml) | Human sputum elastase | Porcine pancreas elastase | Trypsin (bovine) | Chymotrypsin (bovine) | Human leukocyte elastase | Cathepsin G |
|---|---|---|---|---|---|---|
| WS7622A | 0.0071 | <0.005 | >250 | 0.031 | 0.017 | 1.1 |
| WS7622B | 0.038 | 0.013 | >250 | 0.13 | 0.029 | 1.85 |
| WS7622C | 0.12 | 0.036 | >5 | 0.21 | | |
| WS7622D | 0.15 | 0.12 | >5 | 0.38 | | |

2) Inhibitory effect of derivatives of WS7622A substance on human leukocyte elastase

| | µg/ml |
|---|---|
| The compound of Example 2 | 0.0103 |
| The compound of Example 3 | 0.0103 |

Each value was expressed as 50% inhibitory concentration.

Pharmaceutical compositions of this invention can be used in a conventional pharmaceutical forms such as powders, fine granules, granules, tablets, dragee, microcapsules, capsules, suppository, solution, suspension, emulsion, syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, polypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 100 mg to 10 g as the object compound or its pharmaceutically acceptable salt, preferably 1 g to 5 g on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

EXAMPLE 1

Production of WS7622A Substance

An aqueous seed medium (200 ml) containing 1% of soluble starch, 1% of sucrose, 1% of glucose, 1% of pharma media (cotton seed flour, trade name), 0.5% of polypeptone, 0.5% of soybean meal and 0.1% of $CaCO_3$ was poured into each of twelve 500-ml Elrenmyer flasks, and sterilized at 120° C. for 30 min. A loopful of Streptomyces resistomycificus No. 7622 on mature slant culture was inoculated to each of the seed medium. The flasks were shaken on a rotary shaker at 30° C. for 3 days. The resultant seed culture was inoculated to 160l of sterile fermentation medium consist of 4% Pine-Dex (starch acid hydrolysate, trade name), 1% gluten meal, 0.5% wheat germ, 0.5% potato protein and 0.2% $CaCO_3$ in a 200l stainless steel jar-fermentor. The fermentation was carried out at 25° C. for 5 days under aeration of 160l/min and agitation of 200 rpm.

An amount of the WS7622A substance in the fermentation broth was quantified by elastase inhibition assay in vitro. The sample for the assay was prepared as follows;

An equal volume of acetone was added to a broth with vigorous stirring. The mixture was allowed to stand at room temperature for 1 hour and then filtered. The filtrate was concentrated under reduced pressure to an appropriate volume. The elastase inhibition assay was described before.

The cultured broth (160l) was filtered with the aid of diatomaseous earth. Fifty liter of acetone was added to the mycelial cake with stirring. The mixture was allowed to stand at room temperature overnight, and then filtered. The filtrate was concentrated to remove the acetone under reduced pressure. The filtrate (140l) from the broth obtained in the above and the mycelial extract were combined, and then passed through a column of polymeric adsorbent, Diaion HP-20 (trade name, made by Mitsubishi Chemical Industrial Limited, 17l). The column was washed with 50l of water and 50% of aqueous methanol solution (50l), and the adsorbate was eluted with 40l of methanol. The eluate was concentrated under reduced pressure to give an oily residue. The residue was applied to a column chromatography on silica gel (Kiesel gel 60, 70–230 mesh, Merck, 1.3l). The column was washed with 2l of n-hexane-ethyl acetate (1:1, V/V) and 4l of ethyl acetate and the active substance was eluted from the column with acetone (3l) and acetone-methanol (10:1, 6l). The active fractions (6l) were combined and concentrated to dryness, and was subjected to a column chromatography on silica gel with stepwised elution using solvents of chloroform-methanol mixture. The active substance was eluted in chloroform-methanol (10:1, V/V) solution. The fractions were concentrated and dried under reduced pressure to give 3 g of yellow powder. WS7622A substance was separated by High Performance Liquid Chromatography (HPLC). A YMC-D-ODS-15B 30×250 mm stainless steel column (Yamamura Chemical Laboratories, Japan) packed with s-15 reverse phase silica was used. Fifty milligram of the yellow powder was dissolved in 50 µl of methanol and applied to the HPLC with 60% of aqueous methanol solution as mobile phase and flow rate of 20 ml/min. The retention time of WS7622A substance was 17.6 min. The chromatogram was run 60 times, and the fractions containing WS7622A substance were combined and concentrated to dryness. The residue was dissolved with small amount of methanol and allowed to stand over night to give 600 mg of WS7622A substance as colorless prism.

EXAMPLE 2

Production of Dimethylated WS7622A Substance $R^1$, $R^2$ : methyl

To a solution of WS7622A substance (1 g) in a mixture of chloroform (20 ml) and methanol (20 ml) was added trimethylsilyldiazomethane (4 ml, 10% weight in hexane, purchased from Petrarch Systems Co., Ltd.) and the solution was allowed to stand at room temperature overnight. The solution was evaporated to dryness to give an oil which was purified by column chromatography on silica gel eluting with a mixture of chloroform and methanol (95:5). The product fractions were collected and evaporated to dryness. The obtained white residue was triturated with diethyl ether to give 0.62 g of dimethylated WS7622A substance as white powder.

Appearance: white powder
Molecular formula: $C_{49}H_{67}N_9O_{13}$
FAB-MS m/z: 990 $(M+H)^+$
Thin Layer Chromatography (TLC)
Silica gel plate

| (Merck Art 5715) | chloroform-methanol (5:1, V/V) | Rf 0.72 |
|---|---|---|
| | chloroform-methanol (9:1, V/V) | Rf 0.40 |

Specific rotation: $[\alpha]_D^{23} + 37°$ (C=1.6, CHCl$_3$-MeOH (1:1)).

Infrared absorption spectrum: $\nu_{max}^{Nujol}$ 3400, 3250, 1730, 1660, 1640, 1540, 1520, 1330, 1260, 1210, 1180, 1160, 1100, 1080, 1000, 980, 920 cm$^{-1}$

| $^1$H Nuclear magnetic resonance spectrum: (400 MHz, CD$_3$OD) δ ||
|---|---|
| 7.20–7.11 | (3H, m) |
| 6.93 | (1H, s) |
| 6.83 | (1H, q, J=7Hz) |
| 6.77 | (2H, d, J=8Hz) |
| 6.59 | (1H, s) |
| 5.48 | (1H, m) |
| 5.15 | (1H, m) |
| 4.85 | (1H, s) |
| 4.76 | (1H, m) |
| 4.67 | (1H, m) |
| 4.42 | (1H, m) |
| 3.99–3.89 | (2H, m) |
| 3.82 | (3H, s) |
| 3.81 | (3H, s) |
| 3.66 | (1H, m) |
| 3.55 | (1H, m) |
| 3.02 | (1H, m) |
| 2.95 | (3H, s) |
| 2.90 | (1H, m) |
| 2.60–1.94 | (6H, m) |
| 1.82 | (1H, m) |
| 1.77 | (3H, d, J=7Hz) |
| 1.68–1.58 | (4H, m) |
| 1.46 | (3H, d, J=7Hz) |
| 1.13 | (3H, d, J=6Hz) |
| 1.12 | (3H, d, J=6Hz) |
| 1.01 | (3H, d, J=6Hz) |
| 0.96 | (3H, d, J=6Hz) |
| 1.00 | (1H, m) |

EXAMPLE 3

Production of Diacetylated WS7622A Substance ($R^1$, $R^2$ : acetyl)

To a solution of WS7622A substance (1 g) in pyridine (5 ml) was added acetic anhydride (0.24 ml) and the mixture was allowed to stand at room temperature overnight. The mixture was evaporated to dryness to give an oil which was purified by column chromatography on silica gel eluting with a mixture of chloroform and methanol (95:5). Crystallization from hot methanol-isopropyl ether gave 0.73 g of diacetylated WS7622A substance as a white powder.

Appearance: colorless prism
Molecular formula: $C_{51}H_{67}N_9O_{15}$
FAB-MS m/z: 1046 $(M+H)^+$
Thin layer chromatography:
Silica gel plate

| (Merck Art 5715) | chloroform-methanol (5:1, V/V) | Rf 0.73 |
|---|---|---|
| | chloroform-methanol (9:1, V/V) | Rf 0.40 |

Specific rotation: $[\alpha]_D^{23} + 29°$ (C=1.0, CHCl$_3$-MeOH (1:1))

Infrared absorption spectrum: $\nu_{max}^{Nujol}$ 3400, 1770, 1730, 1660, 1640, 1540, 1420, 1340, 1260, 1210, 1080, 1010, 980, 920 cm$^{-1}$

| $^1$H Nuclear magnetic resonance spectrum: (400 MHz, DMSO-d$_6$) δ ||
|---|---|
| 9.48 | (1H, broad signal) |
| 8.37 | (1H, d, J=8Hz) |
| 7.76 | (1H, d, J=7Hz) |
| 7.23–7.10 | (4H, m) |
| 7.18 | (1H, s) |
| 7.03 | (1H, d, J=9Hz) |
| 6.93 | (1H, s) |
| 6.76 | (2H, d, J=8Hz) |
| 6.74 | (1H, br s) |
| 6.65 | (1H, q, J=7Hz) |
| 5.74 | (1H, m) |
| 5.42 | (1H, m) |
| 5.08 | (1H, m) |
| 4.77 | (1H, d, J=10Hz) |
| 4.64 | (1H, m) |
| 4.57 | (1H, m) |
| 4.42 | (1H, m) |
| 3.92–3.78 | (2H, m) |
| 3.49 | (1H, m) |
| 3.34 | (1H, m) |
| 2.90 | (1H, dd, J=13 and 12Hz) |
| 2.80 | (3H, s) |
| 2.70 | (1H, m) |
| 2.60 | (1H, dd, J=13 and 11Hz) |
| 2.54 | (1H, septet, J=6Hz) |
| 2.42–2.27 | (2H, m) |
| 2.27 | (3H, s) |
| 2.25 | (3H, s) |
| 2.17 | (1H, m) |
| 1.88 | (1H, m) |
| 1.70 | (1H, m) |
| 1.66 | (3H, d, J=7Hz) |
| 1.60–1.46 | (4H, m) |
| 1.34 | (3H, d, J=6Hz) |
| 0.99 | (6H, d, J=6Hz) |
| 0.91 | (3H, d, J=6Hz) |
| 0.88 | (3H, d, J=6Hz) |
| 0.90 | (1H, m) |

EXAMPLE 4

Production of WS7622B Substance

An aqueous seed medium (200 ml) containing 1% of soluble starch, 1% of sucrose, 1% of glucose, 1% of pharma media (cotton seed fluor, trade name), 0.5% of polypeptone, 0.5% of soybean meal and 0.1% of CaCO$_3$ was poured into each of twelve 500-ml Elrenmyer flasks, and sterilized at 120° C. for 30 min. A loopful of *Streptomyces resistomycificus* No. 7622 of mature slant culture was inoculated to each of the seed medium. The flasks were shaken on a rotary shaker at 30° C. for 3 days. The resultant seed culture was inoculated to 160l of sterile fermentation medium consist of 4% Pine-Dex {starch acid hydrolyste trade name), 1% gluten meal, 0.5% wheat germ, 0.5% potato protein and 0.2% $CaCO_3$ in a 200l stainless steel jar-fermentor. The fermentation was carried out at 25° C. for 5 days under aeration of 160l/min and agitation of 200 rpm.

An amount of the WS7622B substance in the fermentation broth was quantified by elastase inhibition assay in vitro. The sample for the assay was prepared as follows;

An equal volume of acetone was added to a broth with vigorous stirring. The mixture was allowed to stand at room temperature for 1 hour and then filtered. The filtrate was concentrated under reduced pressure to an appropriate volume. The elastase inhibition assay was described before.

The cultured broth (160l) was filtered with the aid of diatomaseous earth. Fifty liter of acetone was added to the mycelial cake with stirring. The mixture was allowed to stand at room temperature overnight, and then filtered. The filtrate was concentrated to remove the acetone under reduced pressure. The filtrate (140l) from the broth obtained in the above and the mycelial extract were combined, and then passed through a column of polymeric adsorbent, Diaion HP-20 (trade name, made by Mitsubishi Chemical Industrial Limited, 17l). The column was washed with 50l of water and 50% of aqueous methanol solution (50l), and the adsorbate was eluted with 40l of methanol. The eluate was concentrated under reduced pressure to give an oily residue. The residue was applied to a column chromatography on silica gel (Kiesel gel 60, 70-230 mesh, Merck, 1.3l). The column was washed with 2l of n-hexane-ethyl acetate (1:1, V/V) and 4l of ethyl acetate and the active substance was eluted from the column with acetone (3l) and acetone-methanol (10:1, 6l). The active fractions (6l) were combined and concentrated to dryness, and was subjected to a column chromatography on silica gel with stepwised elution using solvents of chloroform-methanol mixture. The active substance was eluted with chloroform-methanol (10:1). The fractions were concentrated and dried under reduced pressure to give 3 g of yellow powder. WS7622B substance was separated by High Performance Liquid Chromatography (HPLC). A YMC-D-ODS-15B 30×250 mm stainless steel column (Yamamura Chemical Laboratories, Japan) packed with s-15 reverse phase silica was used. Fifty milligram of the yellow powder was dissolved in 50 μl of methanol and applied to the HPLC with 60% of aqueous methanol solution as mobile phase and flow rate of 20 ml/min. The retention time of WS7622B substance was 23.0 min. The chromatogram was run 60 times, and the fractions containing WS7622B substance were combined and concentrated, and then crystallized with methanol to give 180 mg of WS7622B substance as colorless needles.

EXAMPLE 5

Production of WS7622C and D Substances

The fermentation was carried out in the same manner as that of Example 1.

To the cultured broth (70 L) thus obtained, seventy liters of methanol were added with stirring. The mixture was allowed to stand at room temperature for 1 hour, and then filtered. One hundred and forty liters of water was added to the filtrate and 280l of 25% aqueous methanol solution was made. The solution was passed through a column of polymeric adsorbent, Diaion HP-20 (trade name, made by Mitsubishi Chemical Industries Limited, 5l). The column was washed with 10l of 50% aqueous methanol solution and eluted with 10l of methanol. The eluate was concentrated under reduced pressure to give an oily residue. The residue was applied to a column chromatography on silica gel (Kiesel gel 60, 70-230 mesh, Merck, 2.2l). The column was washed with 10l of acetone and the active substances were eluted from the column with acetone-methanol (5:1). Fraction collection of the eluate was as follows; fraction No. 1: 1l, fraction No. 2: 5.4l, fraction No. 3: 3.8l, fraction No. 4: 3.2l. WS7622C and D substances were eluted at fraction No. 3 and fraction No. 4, respectively.

Isolation of WS7622C Substance

Fraction No. 3 was concentrated and dried under reduced pressure to give 1.2 g of a yellow powder. One gram of the powder containing WS7622C substance was redissolved in 6 ml of chloroform-methanol (10:1) and subjected to 100 ml of silica gel column, prepacked with chloroform-methanol (10:1). The column was washed with 300 ml of chloroform-methanol (10:1) and WS7622C substance was eluted with chloroform-methanol (5:1). The first 180 ml of the eluate was discarded and subsequent 80 ml were pooled and concentrated and dried under reduced pressure to give 372 mg of powder. The powder was redissolved in 6 ml of ethanol and stand at 4° C. for 1 hour gave 170 mg of WS7622C substance as colorless needles.

Isolation of WS7622D Substance

Fraction No. 4 was concentrated to dryness gave 3.3 g of a yellow powder. One gram of the powder containing WS7622D substance was dissolved in 6 ml of chloroform-methanol (20:1) and subjected to 100 ml of silica gel column, prepacked with chloroform. The column was washed with 300 ml of chloroform-methanol (20:1) and 300 ml of chloroform-methanol (10:1) and WS7622D substance was eluted with chloroform-methanol (5:1). The first 200 ml of the eluate was discarded and subsequent 90 ml were pooled and concentrated to dryness gave 127 mg of powder. The powder was dissolved in a small amount of ethanol and stand at 4° C. overnight gave 90 mg of WS7622D substance as colorless needles.

We claim:

1. A method of treating pulmonary emphysema or adult respiratory distress syndrome in a subject in need thereof which comprises administering to the subject an effective amount of WS7622A, B, C and/or D, or di-lower alkyl derivative of WS7622A substance, or di-lower alkanoyl derivative of WS7622A substance, or their pharmaceutically acceptable salt.

* * * * *